United States Patent
Allen et al.

(10) Patent No.: US 6,168,584 B1
(45) Date of Patent: *Jan. 2, 2001

(54) SPACERS FOR USE IN DISPOSABLE ABSORBENT ARTICLES AND DISPOSABLE ABSORBENT ARTICLES HAVING SUCH SPACERS

(75) Inventors: Patrick Jay Allen, Cincinnati, OH (US); Bret Alan Sims, Ft. Collins, CO (US)

(73) Assignee: The Procter & Gamble Company, Cincinnati, OH (US)

( * ) Notice: This patent issued on a continued prosecution application filed under 37 CFR 1.53(d), and is subject to the twenty year patent term provisions of 35 U.S.C. 154(a)(2).

Under 35 U.S.C. 154(b), the term of this patent shall be extended for 0 days.

(21) Appl. No.: 08/698,471

(22) Filed: Aug. 15, 1996

Related U.S. Application Data (63) Continuation of application No. 08/251,031, filed on May 31, 1994, now abandoned, which is a continuation of application No. 08/136,179, filed on Oct. 15, 1993, now abandoned, which is a continuation of application No. 07/898,047, filed on Jun. 11, 1992, now abandoned.

(51) Int. Cl.$^7$ .................................................. A61F 13/15
(52) U.S. Cl. ............................ 604/385.19; 604/385.31
(58) Field of Search ........................... 604/385.1–387, 604/384–390, 393, 366, 378, 385.01, 385.19, 385.31

(56) References Cited

U.S. PATENT DOCUMENTS

| | | | |
|---|---|---|---|
| Re. 33,351 | * 9/1990 | Papajohn . | |
| 2,043,325 | 6/1936 | Jackson, Jr. . | |
| 2,334,597 | 11/1943 | Badertscher | 267/20 |
| 2,517,269 | 8/1950 | Wolfe | 267/1 |
| 3,881,488 | * 5/1975 | Delanty et al. | 604/374 |
| 4,212,302 | * 7/1980 | Karami | 604/374 |
| 4,324,247 | * 4/1982 | Aziz | 604/374 |
| 4,382,443 | 5/1983 | Shafer et al. | 604/396 |
| 4,560,380 | 12/1985 | Tharel . | |
| 4,662,877 | 5/1987 | Williams . | |
| 4,731,065 | 3/1988 | Yamada | 604/355 |
| 4,778,459 | 10/1988 | Fuisz | 604/378 |
| 4,804,380 | * 2/1989 | Lassen et al. | 604/393 |
| 4,834,737 | 5/1989 | Khan | 604/385.2 |
| 4,865,597 | * 9/1989 | Mason, Jr. et al. . | |
| 4,892,536 | 1/1990 | Desmarais et al. | 604/385.2 |
| 4,895,568 | 1/1990 | Enloe | 604/385.2 |

(List continued on next page.)

FOREIGN PATENT DOCUMENTS

| | | |
|---|---|---|
| 0355740 | 2/1990 | (EP) . |
| 0486006 | 5/1992 | (EP) . |
| 2495899 | 6/1982 | (FR) . |
| 2561078 | 9/1985 | (FR) . |
| 2042342 | 9/1980 | (GB) . |
| 2074875 | 11/1981 | (GB) . |
| 90/14063 | 11/1990 | (WO) . |
| 92/15269 | 9/1992 | (WO) . |

*Primary Examiner*—John G. Weiss
*Assistant Examiner*—K. M. Reichle
(74) *Attorney, Agent, or Firm*—Jay A. Krebs; Larry L. Huston; David M. Weirich (57) ABSTRACT

A spacer for use in a disposable absorbent article. The spacer is symmetric about a longitudinal axis and has two transversely oriented springs generally orthogonal to the longitudinal axis. The transversely oriented springs have different spring rates, so that transverse compression caused by the wearer's thighs may be readily accommodated, yet the spacer remain open to receive fecal material. The spacer may be advantageously used in a disposable absorbent article having a void space between the topsheet and the core, and maintain this void space under the weight of the wearer.

11 Claims, 2 Drawing Sheets

U.S. PATENT DOCUMENTS

| | | | |
|---|---|---|---|
| 4,962,916 | 10/1990 | Palinkas | 267/153 |
| 4,968,312 | 11/1990 | Khan . | |
| 4,990,147 | 2/1991 | Freeland | 604/385.2 |
| 5,062,840 | 11/1991 | Holt et al. | 604/385.1 |
| 5,171,236 | 12/1992 | Dreier et al. | 604/369 |
| 5,176,672 | 1/1993 | Bruemmer et al. | 604/385.1 |
| 5,330,459 | 7/1994 | Lavon et al. | 604/385.1 |
| 5,391,160 | 2/1995 | Runeman et al. | 604/378 |
| 5,520,674 | 5/1996 | Lavon et al. | 604/385.1 |

\* cited by examiner

SPACERS FOR USE IN DISPOSABLE ABSORBENT ARTICLES AND DISPOSABLE ABSORBENT ARTICLES HAVING SUCH SPACERS

This is a continuation of application Ser. No. 08/251,031, filed on May 31, 1994 which is a continuation Application of Ser. No. 08/136,179, filed Oct. 15, 1993, which is a continuation Application of Ser. No. 07/898,047, filed Jun. 11, 1992, all now abandoned.

FIELD OF THE INVENTION

The present invention relates to a spacer for use in disposable absorbent articles, particularly to spacers for use in disposable absorbent articles which isolate fecal material from the wearer, and more particularly to spacers for use in disposable absorbent articles having a void space for receiving the fecal material, wherein the void space is maintained by such a spacer. The present invention also relates to disposable absorbent articles having such spacers.

BACKGROUND OF THE INVENTION

Disposable absorbent articles are well known in the art. Disposable absorbent articles are used to absorb and retain urine and fecal material. A particularly desired feature of disposable absorbent articles is the capability to minimize the task of cleaning of fecal material which is present on the wearer's skin after the soiled disposable absorbent article is removed from the wearer. In order to achieve this end, and to minimize epidermal contact and the associated irritation caused by the fecal material, attempts have been made to confine the fecal material to limited portions of the disposable absorbent article.

Selected teachings in the art disclose a cavity or cutout in the absorbent core to receive the fecal material. The fecal material passes through the topsheet and is received by the material removed from or otherwise displaced from the absorbent core (such as through compression). However, these references suffer from the drawback that a cavity in the core or a removal of material from the core decreases its absorbent capacity. The cavity is limited in volume by the size of the core. Furthermore, the cavity may not remain registered with the anal opening. Examples of such teachings include U.S. Pat. No. 2,043,325 issued Jun. 9, 1936 to Jackson, Jr., U.S. Pat. No. 4,731,065 issued Mar. 15, 1988 to Yamada, U.S. Pat. No. 4,834,737 issued May 30, 1989 to Khan, and U.S. Pat. No. 5,062,840 issued Nov. 5, 1991 to Holt et al.

One attempt to minimize the task of cleaning of fecal material from the skin of the wearer is to provide a void space in the disposable absorbent article to receive the fecal material and to isolate it from the skin of the wearer. Typically, the void space is intermediate the topsheet which contacts the skin of the wearer and the absorbent core which absorbs fluid excretions, such as urine. In this arrangement, the topsheet may have an aperture or other passageway which communicates the fecal material into the void space.

Many of these references also disclose various arrangements for providing elastic extensibility to the topsheet relative to the aperture therethrough and the absorbent core. However, these references suffer from the drawback that the void space for receiving fecal material typically does not remain open when the wearer is in a sitting position or after the first loading has occurred. Examples of such teachings include U.S. Pat. No. 4,662,877 issued May 5, 1987 to Williams, commonly assigned U.S. Pat. No. 4,892,536 issued Jan. 9, 1990 to Desmarais et al., and commonly assigned U.S. Pat. No. 4,990,147 issued Feb. 5, 1991 to Freeland.

To overcome this problem, other references teach adding a spacer to the disposable absorbent article. The spacer may be transversely oriented, generally horse-shoe shaped, or may comprise longitudinally oriented parallel or divergent members.

However, these references suffer from the drawback that the spacer is not disposed in a void space, or if so disposed, is constructed such that transverse compression caused by the wearer's thighs may close the spacer, preventing fecal material from passing through the aperture in the topsheet to the void space. Instead, the fecal material remains on the topsheet and in contact with the skin of the wearer.

Examples of such references include European Patent Application No. 0,355,740 A2 published Feb. 28, 1990 in the name of Enloe, UK Patent Application No. GB2,074,875 A published Nov. 11, 1981 in the name of Edwards, French Patent Application No. 2,561,078 published Sep. 20, 1985 in the name of Lefebvre, U.S. Pat. No. 4,382,443 issued May 10, 1983 to Shafer et al., and U.S. Pat. No. 4,560,380 issued Dec. 24, 1985 to Tharel.

A need exists in the art for a spacer which can be incorporated into a disposable absorbent article and particularly into a disposable absorbent article having a void space. Furthermore, a need exists for a spacer which can accommodate the natural transverse compression caused by the wearer's thighs. Yet further, such a spacer and the disposable absorbent article used therewith, should not become misregistered with the anal opening nor unduly restrict the target area for receipt of fecal material while the spacer and disposable absorbent article are worn.

Accordingly, it is an object of this invention to provide a spacer which is adaptable to a wide variety of disposable absorbent articles and particularly disposable absorbent articles having a void space, which can accommodate the transverse pressure imposed by the wearer's thighs, can remain properly registered during use, and which does not unduly restrict the target area for the receipt of fecal material while the disposable absorbent article is worn.

SUMMARY OF THE INVENTION

The invention comprises a spacer for use in a disposable absorbent article having front and rear waist margins and longitudinal and transverse axes. The spacer symmetric about the longitudinal axis. The spacer may comprise a smaller and a larger transverse span disposed respectively at longitudinally opposite ends of the spacer, with the larger span disposed toward the rear waist margin. Alternatively, the spacer may comprise a generally closed figure having a greater and a lesser radii of curvature at respective longitudinally opposite ends, each radius having a concavity oriented in the longitudinal direction and defining portions spanning the longitudinal axis, these portions being joined by longitudinally oriented spans of the spacer.

The spacer may be incorporated into a disposable absorbent article comprising a liquid impervious backsheet, a liquid previous topsheet at least partially peripherally joined to the backsheet to form a void space intermediate the topsheet and backsheet, and an absorbent core disposed between the topsheet and backsheet. The absorbent core comprises and upper layer joined to the topsheet and a lower layer joined to the backsheet. The spacer is joined to either the upper layer or the lower layer of the absorbent core in a disposition intermediate the upper layer and the lower layer such that the upper layer and the lower layer have a space therebetween of at least about 0.6 centimeters when the spacer is under a pressure of about 1,400 kilograms per square meter. The topsheet has an aperture register with the spacer for communicating liquid and solid fecal material to the void space unoccupied by the absorbent core and the spacer. The lower layer of the absorbent core comprises air felt disposed intermediate the spacer and the backsheet and devoid of a cavity or cutout therein registered with void space.

BRIEF DESCRIPTION OF THE DRAWINGS

While the Specification concludes with claims particularly pointing out and distinctly claiming the present invention, it is believed the same will be better understood from the following description taken in conjunction with the associated drawings in which like reference numerals represent the same component and:

DETAILED DESCRIPTION OF THE INVENTION

Figure 1:
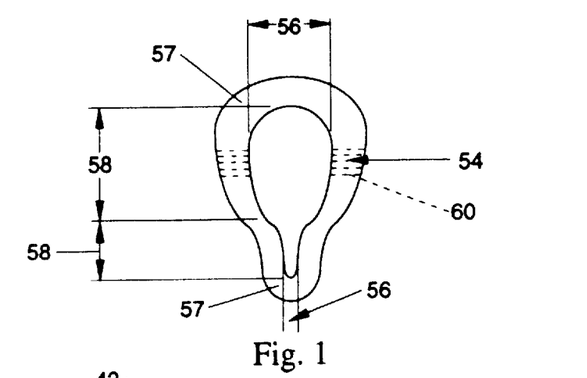
FIG. 1 is a top plan view of a spacer according to the present invention.

Referring to FIG. 1, a "spacer" refers to a component of a disposable absorbent article 20 which separates two other components of the disposable absorbent article 20 to provide a desired clearance between such components. The spacer 54 may, although not necessarily, form a generally closed figure. The spacer 54 has a finite thickness and is symmetric about a longitudinal axis LL. The spacer 54 is provided with dual stiffnesses, representing spring rates oriented in a transverse direction generally orthogonal the longitudinal axis LL and lying within the plane of the spacer 54. More particularly, the spacer 54 has dual spring rates, or two different deflections in response to unit forces transversely applied to the perimeter of the spacer 54 in a transverse direct ion oriented towards the longitudinal axis LL.

Figure 2:
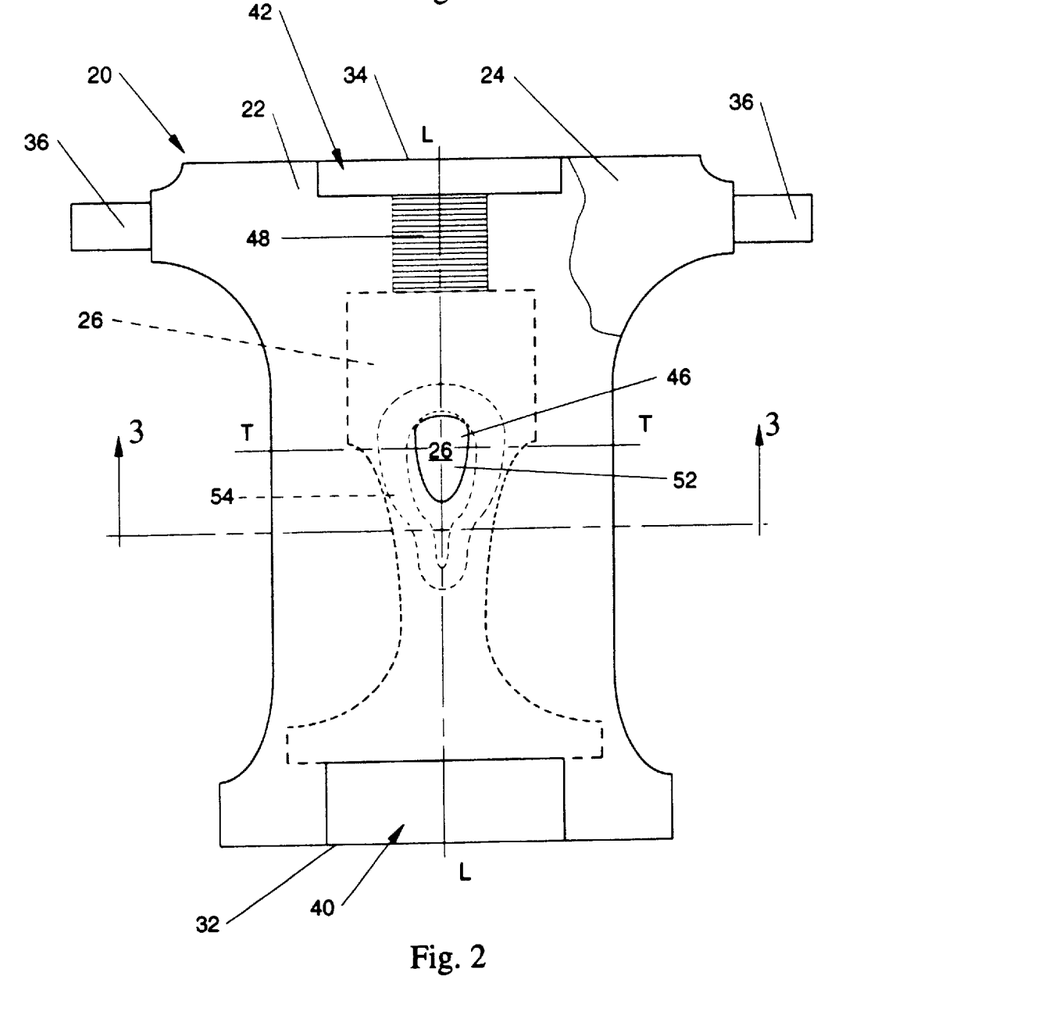
FIG. 2 is a top plan view of a disposable absorbent article shown partially in cutaway and incorporating the spacer of FIG. 1 and an absorbent core in phantom.

Referring to FIG. 2, a "disposable absorbent article" refers to a garment worn about the body of a wearer which collects body exudates. The disposable absorbent article 20 is intended to be discarded after a single use, and not laundered or otherwise restored (although certain components may be recycled or composted).

A preferred disposable absorbent article 20 according to the present invention comprises a diaper to be worn by an infant. The disposable absorbent article 20 comprises a liquid previous topsheet 22, a liquid impervious backsheet 24, and an absorbent core 26 intermediate the topsheet 22 and the backsheet 24. The topsheet 22 and the backsheet 24 are at least partially peripherally joined to ensure the core 26 is held in the desired position. As further described in reference to FIG. 4, the core 26 may comprise two layers, an upper layer 26U juxtaposed with the topsheet 22 and a lower layer 26L Juxtaposed with the backsheet 24.

Figure 3:
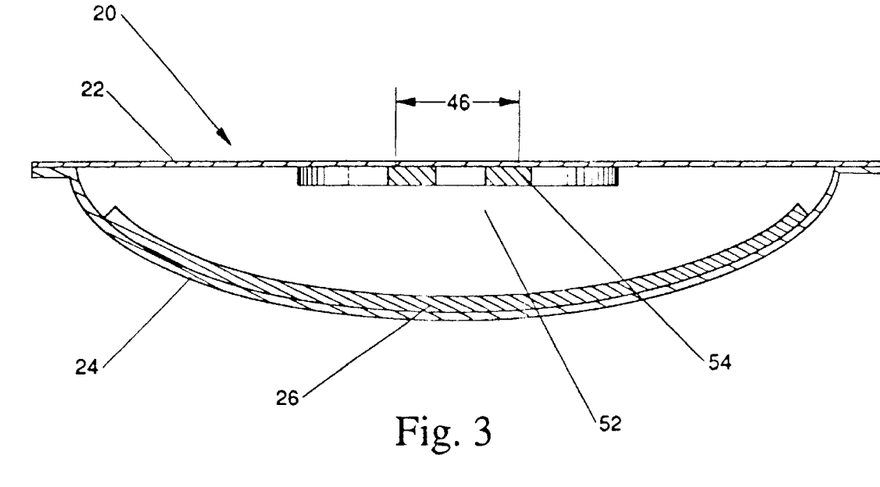
FIG. 3 is a vertical sectional view taken along line 3—3 of FIG. 2.
Figure 4:
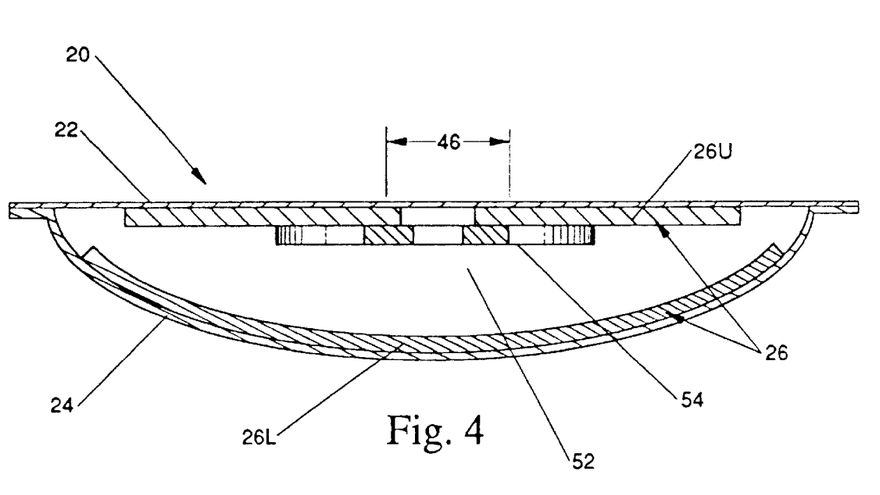
FIG. 4 is a vertical sectional view of a disposable absorbent article having an upper core layer and a lower core layer.

As illustrated in FIG. 3, the disposable absorbent article 20 according to the present invention may further comprise a spacer 54 according to the present invention and disposed between the underside of the topsheet 22 and the backsheet 24 and preferably disposed between the underside of the topsheet 22 and the lower layer 26L of the core 26. More preferably, as illustrated in FIG. 4, the spacer 54 is disposed between the underside of the upper layer 26U of the core 26 and the lower layer 26L of the core 26.

As illustrated in FIG. 2, a disposable absorbent article 20 according to the present invention may further comprise elastic leg cuffs and/or barrier leg cuffs to prevent leakage of body exudates through the leg openings of the disposable absorbent article 20 while it is worn. A disposable absorbent article 20 according to the present invention preferably further comprises an elastic waist band to provide for improved fit about the waist of the wearer. A disposable absorbent article 20 according to the present invention may further comprise adhesive tape fasteners 36 juxtaposed with the rear portion 42 and a fastening surface juxtaposed with the front portion 40 of the disposable absorbent article 20 to conveniently secure the disposable absorbent article 20 about the waist of the wearer. For clarity, the elastic leg cuffs, barrier leg cuffs, and elastic waist band are omitted from the figures.

However, if it is desired to incorporate such components into the disposable absorbent article 20, reference is made to commonly assigned U.S. Pat. No. 4,081,301 issued Mar. 28, 1978 to Buell which discloses a method and apparatus for applying elastic strands to a disposable absorbent article 20 to make leg cuffs; commonly assigned U.S. Pat. No. 4,909,803 issued Mar. 20, 1990 to Aziz et al. which shows how to incorporate barrier leg cuffs into a disposable absorbent article 20; commonly assigned U.S. Pat. No. 3,848,594 issued Nov. 19, 1974 to Buell which discloses how to make and incorporate adhesive tape fasteners into a disposable absorbent article 20; and commonly assigned U.S. Pat. No. 4,816,025 issued Mar. 28, 1989 to Foreman which discloses how to make a suitable waist band for a disposable absorbent article 20. The disclosures of these four patents are incorporated herein by reference for the purpose of showing how to advantageously incorporate these optional features into a disposable absorbent article 20 according to the present invention.

FIG. 2 illustrates a disposable absorbent article 20 according to the present invention laid out in a flat state having no elastic induced contraction. The topsheet 22 and the backsheet 24 generally define the periphery of the disposable absorbent article 20. The periphery is the outer perimeter and greatest extent of the disposable absorbent article 20. The periphery comprises a front waist margin 32, a rear waist margin 34, and two longitudinal side margins.

The front waist margin 32 and rear waist margin 34 are those portions of the disposable absorbent article 20 which, when worn, encircle the waist of the wearer and are generally at the highest elevation of the disposable absorbent article 20 when the wearer is in the standing position. The longitudinal side margins are those portions of the disposable absorbent article 20 periphery which connect the front and rear waist margins 32 and 34. The crotch of the disposable absorbent article 20 is that portion of the disposable absorbent article 20 which is disposed between the front waist margin 32 and rear waist margin 34 and which, when worn, is typically between the legs of the wearer.

The core 26 of the disposable absorbent article 20 does not extend into the front waist margin 32 or rear waist margin 34, so that the topsheet 22 and backsheet 24 may be joined and sealed to each other in this area or may be joined and sealed to each other in other areas. Preferably, the front and rear waist margins 32 and 34 longitudinally extend about five percent of the longitudinal dimension of the disposable absorbent article 20 from the edge of the disposable absorbent article 20 towards the transverse axis of the disposable absorbent article 20.

As used herein, the "longitudinal" dimension, direction or axis of the disposable absorbent article 20 is that dimension, direction or axis LL which is aligned front to back with respect to the wearer as the disposable absorbent article 20 is worn. The longitudinal axes LL of the spacer 54 and the disposable absorbent article 20 are preferably coincident when the spacer 54 is incorporated into the disposable absorbent article 20.

The "transverse" dimension, direction or axis of the disposable absorbent article 20 is orthogonal the longitudinal direction and sideways aligned as the disposable absorbent article 20 is worn. The transverse axis TT divides the disposable absorbent article 20 into front and rear portions 40 and 42, corresponding in position to the respective front and rear waist margins 32 and 34. The "Z-direction" is orthogonal both the longitudinal and transverse directions, and does not lie within the plane of the disposable absorbent article 20 or within the plane of the spacer 54.

The embodiment described herein is suitable for a wearer weighing about 7.3 kilograms to about 12.2 kilograms (16 to 27 pounds) and having ischia bones spaced about 3.0 centimeters to about 7.6 centimeters (1.2 to 3.0 inches) apart. It will be understood that if the spacer 54 and disposable absorbent article 20 are intended for use with smaller or larger sized wearers, including adults, the disposable absorbent article 20 and spacer 54 will have to be scaled accordingly.

One nonlimiting example of spacer 54 sized to fit the aforementioned range of wearers may be made having a thickness in the Z-direction of about 1.3 to about 1.9 centimeters (0.5 to 0.75 inches) and an overall longitudinal dimension of about 8.9 to about 11.8 centimeters (3.5 to 4.6 inches) and a transverse opening of about 1.9 centimeters (0.75 inches). Such a spacer 54 may also have an overall transverse dimension at the perimeter of the end of the spacer 54 intended for disposition towards the front waist margin 32 of the disposable absorbent article 20 of about 4.9 centimeters (1.93 inches) and an overall transverse dimension at the perimeter of the end of the spacer 54 intended to be oriented towards the rear waist margin 34 of about 9.53 centimeters (3.75 inches). This spacer 54 may have a radial thickness ranging from about 1.14 centimeters (0.45 inches) at the smaller end of the spacer 54 to a radial thickness of about 2.8 centimeters (1.1 inches) at the larger end of the spacer 54.

A disposable absorbent article 20 sized to fit the aforementioned range of wearers may be made having a topsheet 22 with a longitudinal dimension of about 43.8 centimeters (17.25 inches) and a backsheet 24 having a longitudinal dimension of about 46.4 centimeters (18.25 inches). As illustrated in FIG. 3, the difference in longitudinal dimension between the topsheet 22 and the backsheet 24 foreshortens the topsheet 22 relative to the backsheet 24 creating a void space 52 therebetween, even when a core 26 is interposed between the topsheet 22 and the backsheet 24. The topsheet 22 and backsheet 24 according to the present invention have a transverse dimension, at the crotch, of about 15.9 centimeters (6.25 inches) and about 21.3 centimeters (8.4 inches) respectively.

The elements of the disposable absorbent article 20 may be assembled in any variety of configurations well known to one skilled in the art. Preferred configurations are described in commonly assigned U.S. Pat. No. 3,860,003 issued Jan. 14, 1975 to Buell, and the aforementioned commonly assigned U.S. Pat. No. 4,909,803 issued Mar. 20, 1990 to Aziz et al., which patents are incorporated herein by reference for the purpose of disclosing well known and preferred disposable absorbent article 20 configurations. In an even more preferred embodiment the configuration of the disposable absorbent article 20 conforms to the teachings of U.S. patent application Ser. No. 07/715,152 filed Jun. 13, 1991 in the name of Buell et al.

Examining the components of the disposable absorbent article 20 in more detail, the topsheet 22 and backsheet 24 are generally coextensive and at least partially peripherally joined together as noted above. As used herein the term "join" refers to the condition where a first member or component is affixed or connected to a second member or component, either directly, or indirectly where the first member or component is affixed or connected to an intermediate member or component which in turn is affixed or connected to the second member or component. The association between the first member or component and the second member or component is intended to remain for the life of the disposable absorbent article 20.

The topsheet 22 and backsheet 24 may be joined by any means well known in the art, such as adhesive bonding or heat sealing. A particularly preferred method of joining the topsheet 22 and backsheet 24 is using hot-melt adhesive such as manufactured by Century Adhesives, Inc. of Columbus, Ohio and marketed as Century 5227 or HL1258 adhesive sold by the H. B. Fuller Company of St. Paul, Minnesota. In a particularly preferred embodiment, adhesive joining is accomplished by longitudinally oriented adhesive bands.

As used herein the "core" refers to any component of the disposable absorbent article 20 used for absorbing and retaining body exudates. The absorbent core 26 may have opposed major faces and may, if desired, be encased by one or more layers of tissue (not shown), or may be coated with a release agent to reduce friction against the fecal material.

The tissue layer, if present, improves the tensile strength of the absorbent core 26 and reduces its tendency to split or clump when wetted. The tissue layer may further improve transverse wicking of fluids and more evenly distribute absorbed liquids throughout the absorbent core 26. A tissue layer having a basis weight of approximately 16 grams per square meter (10 pounds per 3,000 square feet) and an air permeability of approximately 30 cubic meters per minute per square meter (100 cubic feet per minute per square foot) and a differential pressure of 13 millimeters of water (0.5 inch of water) has been found to work well. Alternatively, the topsheet 22 may separately or also wrap around the core 26.

The absorbent core 26 may be made from a variety of commonly used materials such as comminuted wood pulp, typically referred to as air felt. If desired, the absorbent core 26 may further contain absorbent gelling materials as is commonly used in the art. In particular, the absorbent core 26 may be made in accordance with the teachings of commonly assigned U.S. Pat. No. 4,610,678 issued Sep. 9, 1986 to Weisman et al., which patent is incorporated herein by reference for the purpose of showing how to make an absorbent core 26 suitable for use with the present invention. Absorbent gelling materials made in accordance with commonly assigned U.S. Pat. No. Re. 32,649 issued Apr. 19, 1988 to Brandt et al. have been found suitable for use in a disposable absorbent article 20 according to the present invention.

If desired, in a particularly preferred embodiment the lower layer 26L of the absorbent core 26 may have discrete storage and acquisition zones. The storage zone has a higher average density and higher average basis weight than the acquisition zone, so that the acquisition zone may effectively and efficiently acquire rapidly discharged liquids and transport the same to the storage zone for long term containment. Such a lower layer 26L may be made in accordance with the teachings of commonly assigned U.S. Pat. No. 4,834,735 issued May 30, 1989 to Alemany et al., which patent is incorporated herein by reference for the purpose of showing how to make a particularly preferred lower layer 26L of the core 26. One suitable core 26 material is a fibrous absorbent gelling material such as is sold under the tradename Fibersorb by the Atlantic Richfield Company of Los Angeles, Calif.

As illustrated in FIG. 4, the absorbent core 26 may comprise two separate layers, an upper layer 26U which is joined to the underside of the topsheet 22 and a lower layer 26L which is joined to the upper side of the backsheet 24. The absorbent core 26 has longitudinal and transverse dimensions generally less than those of the topsheet 22 and the backsheet 24. The lower layer 26L of the absorbent core 26 may be made of a variety of sizes and shapes, such as rectangular or hourglass. The upper layer 26U of the core 26 generally matches the shape of the rear portion 42 of the topsheet 22. Of course, a single layer core 26, as is well known in the art may be utilized.

The upper and lower layers 26U and 26L of the core 26 may be adhesively joined to the topsheet 22 and backsheet 24, respectively, or joined thereto by any attachment means well known in the art. Particularly preferred attachment means are adhesive spirals and longitudinal and transverse bands of adhesive. Particularly preferred types of adhesive are manufactured by Century Adhesives, Inc. of Columbus, Ohio as Century 5227, HL-1258 Adhesive sold by the H. B. Fuller Company of St. Paul, Minn. and XPO-9-035 adhesive manufactured by the Minnesota Mining and Manufacturing Company of St. Paul, Minn.

Preferably, the lower layer 26L of the core 26 extends the entire longitudinal dimension of the disposable absorbent article 20 between the front waist margin 32 and the rear waist margin 34, but does not intrude into either the front waist margin 32 or the rear waist margin 34. The upper layer 26U of the core 26 need only be present in the rear portion 42 of the disposable absorbent article 20.

One opposed face of the lower layer 26L of the core 26 is oriented towards the upper core 26 layer and the underside of the topsheet 22. The other opposed face of the lower layer 26L of the core 26 is oriented towards the backsheet 24, and preferably is in contacting relationship therewith. More preferably, the lower layer 26L of the absorbent core 26 is adhesively joined to the backsheet 24.

The upper layer 26U of the core 26 insulates the wearer from the impression and applied pressures of the spacer 54, discussed below, which occur when the wearer is sitting while wearing the disposable absorbent article 20. For this reason, the upper layer 26U of the core 26 should be present in at least the rear portion 42 of the disposable absorbent article 20 and particularly, but only present between the rear waist band and the aperture 46. It is not necessary that the upper layer 26U of the core 26 be present in the front portion 40 of the disposable absorbent article 20, because in a preferred embodiment the core 26 has sufficient absorptive capacity without requiring an upper layer 26U of the core 26 in the front portion 40 of the disposable absorbent article 20.

Preferably, the exposed faces of the upper layer 26U and the lower layer 26L (those faces not attached to the topsheet 22 or the backsheet 24 respectively) are well defined and do not intrude into the void space 52. Intrusion of a significant quantity of loose fibers into the void space 52 from the core 26 could interrupt (if not block) the transport of fecal material in the longitudinal direction, and prevent the isolation of such fecal material from the skin of the wearer.

Referring back to FIG. 2, the "topsheet" refers to any liquid pervious facing of the disposable absorbent article 20 which contacts the skin of the wearer while the disposable absorbent article 20 is worn and prevents substantial contact of the core 26 with the skin of the wearer. The topsheet 22 is preferably compliant, tactilely pleasant and nonirritating to the skin of the wearer. Preferably the topsheet 22 is treated to be hydrophilic, to more readily transport body exudates to the core 26.

A suitable topsheet 22 may be manufactured from materials such as porous foams, apertured plastic films, natural fibers (e.g. wood fibers or cotton fibers), synthetic fibers (e.g. polyester or polypropylene fibers) or a combination of the foregoing. A particularly preferred topsheet 22 comprises polypropylene fibers having a denier of about 2.2 and a length of about 15.9 millimeters (0.62 inches). The topsheet 22 may be manufactured according to a number of techniques and may be woven, nonwoven, spunbonded, carded, etc.

A particularly preferred topsheet 22 is carded and thermally bonded and has a weight of about 18 to about 25 grams per square meter, a minimum dry tensile strength of about 400 grams per centimeter taken in the machine direction and a minimum wet tensile strength of at least about 55 grams per square centimeter taken in the cross machine direction. A suitable topsheet 22 is marketed by Veratec, Inc., Division of International Paper Company of Walpole, Mass. under the designation P-8.

Preferably, the topsheet 22 has an elastic panel 48 intermediate the transverse axis and the rear waist margin 34. The elastic panel 48 maintains the topsheet 22 close to the wearer, helping to maintain registration of the aperture 46 with the anal opening. The elastic panel 48 may be incorporated according to the teachings of commonly assigned U.S. Pat. No. 5,032,120 issued Jul. 16, 1991 to Freeland et al., which patent is incorporated herein by reference for the purpose of showing how to make material suitable for the elastic panel 48 and incorporate the elastic panel 48 into the topsheet 22.

If present, the elastic panel 48 is preferably transversely centered on the longitudinal axis, and may transversely extend between the entire longitudinal side margins of the disposable absorbent article 20 or may only be about 3.8 to about 4.5 centimeters (1.5 to 1.8 inches) in width. The elastic panel 48 may longitudinally extend from the rear waist margin 34 to the aperture 46. The elastic panel 48 is preferably about 1.3 centimeters (0.5 inches) in longitudinal dimension in an unstretched condition, and may be extended about 300 percent to a longitudinal dimension of about 5.1 centimeters (2.0 inches) when incorporated into the topsheet 22.

The material comprising the elastic panel 48 should extend about 200 percent under about 6 to about 8 grams of applied loading per 0.03 millimeters (0.001 inches) of thickness per unit centimeter (0.4 inches) of width. A particularly preferred elastic panel 48 may be made according to the teachings of commonly assigned U.S. Pat. No. 5,037,416 issued Aug. 6, 1991 to Allen et al., which patent is incorporated herein by reference for the purpose of illustrating a particularly preferred material of construction for the elastic panel 48.

The pervious topsheet 22 further comprises an aperture 46 centered on the longitudinal axis LL. The aperture 46 may be of any shape desired with a suitable shape being an oval having a longitudinal dimension of about 5.1 centimeters (2.0 inches) and a transverse dimension of about 3.8 centimeters (1.5 inches). The rearwardmost edge of the aperture 46 is disposed at least about 15.2 centimeters (6.0 inches), and preferably about 17.8 centimeters (7.0 inches) to about 21.6 centimeters (8.5 inches) from the rear edge of the disposable absorbent article 20 while it is worn. Alternatively, the aperture 46 may be circular, having a dimension of about 4.13 centimeters (1.625 inches), and centered about 22.38 centimeters (8.813 inches) from the rear waist margin 34. Alternatively, the aperture 46 may be sized, shaped, and registered to match the inside of the spacer 54 according to the present invention.

The aperture 46 provides a passageway for the communication of fecal material from the anal opening through the topsheet 22 into the void space 52. Preferably absorbent gelling materials are not registered with the aperture 46, so that gell-blocking does not occur when large volume urine loading occurs. Gell-blocking may cause the lower layer 26L to block the void space 52 and interrupt the transport of fecal material towards the rear waist margin 34.

The backsheet 24 is impervious to fluids, such as urine, and prevents fluids absorbed by and contained in the absorbent core 26 from wetting undergarments, clothing and bedding. As used herein the "backsheet" refers to any barrier disposed outwardly of the core 26 as the disposable absorbent article 20 is worn and which contains absorbed liquids within the disposable absorbent article 20. Preferably the backsheet 24 is flexible, compliant and readily conforms to the general shape and contour of the wearer's body.

The backsheet 24 may be a polyolefinic film, such as polyethylene, is having a thickness of about 0.01 millimeters to about 0.051 millimeters (0.0005 to 0.002 inches). If desired, the backsheet 24 may be embossed or matte finished to provide a cloth-like appearance or provided with passages to permit vapor escape. A suitable backsheet 24 can be made from a blend of about 45 to 90 percent linear low density polyethylene and about 10 to 55 percent polypropylene. Exemplary backsheet 24 films are sold by Tredegar Industries, Inc. of Terre Haute, Ind. under the designation RR8220 blend for blown films and RR5475 blend for cast films.

As noted above and with reference back to FIG. 1, the spacer 54 comprises two transversely oriented springs. The springs have mutually different spring rates. The spacer 54 is intended to be used so that the transversely oriented spring disposed towards the rear waist margin 34 when the spacer 54 is incorporated into a disposable absorbent article 20 has a greater spring rate than the transversely oriented spring disposed towards the front waist margin 32. However, it is to be recognized that prophetically a disposable absorbent article 20 may be constructed and arranged so that a spacer 54 having dual transversely oriented springs with mutually different spring rates may be employed with the spring having the greater spring rate disposed towards the front waist margin 32.

As used herein, the term "spring rate" refers to the amount of force necessary to apply to the spring to obtain a unit deflection in a particular direction. Conceptually the spring rate may also be thought of as the amount of deflection the spring assumes in response to the application of a unit force in a particular direction. It is to be recognized that the deflection of the spacer 54 must be locally measured at or near the application of the force, because different portions of the spacer 54 will undergo different deflections, due to the two spring rates incorporated into the spacer 54. However, in a spacer 54 according to the present invention, different portions of the spacer 54 will undergo different deflections, which deflections are unequal to those which could occur if only one spring rate was present in the spacer 54.

The dual spring rates within the spacer 54 may be provided by having a spacer 54 with two radii of curvature, a smaller radius of curvature longitudinally disposed towards one end of the spacer 54 and a larger radius of curvature longitudinally towards the other end of the spacer 54. Generally, the longitudinal end of the spacer 54 having the larger radius of curvature will have a greater spring rate, due to the larger transversely oriented span 56 located at this end of the spacer 54. Conversely, the end of the spacer 54 having the smaller radius of curvature will have a lesser spring rate due to the smaller longitudinally oriented span 58 found at this end of the spacer 54 and connecting this end of the spacer 54 to the opposite end.

Without being bound by any theory, the springs incorporated into the embodiment of the spacer 54 described herein are based upon the principle that a linear member, including both rectilinear and relatively short curvilinear executions of linear members, may have a very high spring rate (in compression) along the length of such members. However, the same members will have a much lesser spring rate in a direction generally orthogonal the length of such members.

As noted above, it is generally preferred that when the spacer 54 is incorporated into a disposable absorbent article 20, the spacer 54 is longitudinally disposed so that the end having the smaller radius of curvature and the smaller longitudinally oriented span 58 is oriented towards the front waist margin 32 and the end having the larger radius of curvature and the greater transverse span 56 is oriented towards the rear waist margin 34. This arrangement provides for comfortably accommodating the thighs of the wearer, due to the smaller transverse span 56 at the end of the spacer 54 having the smaller radius of curvature.

It is generally preferred that the spacer 54 selected for incorporation into the disposable absorbent article 20 be a closed figure, so that undesired total collapse does not occur or that an excessively wide spacer 54 is not necessary to prevent undesired total collapse from occurring. It is to be recognized that a spacer 54 may form a nearly closed figure or a figure which has a relatively minor interruption in its circumference and particularly, an interruption which closes upon the application of transverse forces and still the spacer 54 be suitable for use with the claimed invention by performing the same function, in the same way, to achieve the same result.

The radius of curvature of any particular sector of the spacer 54 is determined as follows: the center of curvature of any arc is found using known mathematical means, such as the intersection of the perpendicular bisectors of two chords. The radius is measured from this center to the midpoint of the spacer 54 which is radially halfway between the inner and outer surfaces of the spacer 54. The radius of curvature may change continuously or remain constant throughout any azimuthal position of the spacer 54. Of course, it is to be recognized that the spacer 54 may have at least two centers of curvature. It is to be recognized that a spacer 54 having sharp corners and vertices instead of curvilinear transitions 57 between the transverse and longitudinal spans 56 and 58 oriented in the longitudinal and transverse dimensions may be utilized as well.

The spacer 54 described herein has several radii of curvature. Typically, some of these radii are oriented concave towards the center of the spacer 54 and others are oriented convex towards the center of the spacer 54. The larger and "smaller" radii of curvature refer to the greater and lesser radii of the spacer 54 coincident the longitudinal axis LL, respectively.

The larger radius of curvature of the spacer 54 is preferably greater than or equal to about 3.6 centimeters (1.4 inches), for the embodiment described herein. The smaller radius of curvature of the spacer 54 is preferably less than or equal to about 1.5 centimeters (0.6 inches) for the embodiment described herein. The radii of curvature may vary about ±20 percent from those described herein, and still be suitable for the embodiment described herein. Generally, as the wearer becomes heavier, a spacer 54 having a stiffer transverse span 56 and hence a greater transverse spring rate is preferred, so that more resistance to transverse deflection is provided.

A spacer 54 having the aforementioned radii of curvature and made of the high internal phase emulsion foam described below, may have a constant Z-direction thickness of about 0.64 centimeters to about 1.9 centimeters (0.25 to 0.75 inches) and is preferably about 1.27 centimeters (0.5 inches) in the Z-direction for the embodiment described herein. Generally, as the spacer 54 becomes thicker in the Z-direction, isolation performance improves, at the expense of comfort.

The disclosed spacer 54 may be used alone, or stacked in conjunction with any other desired spacer, to provide a minimum Z-direction free space of at least about 0.64 centimeters (0.25 inches) between the lower layer 26L and the upper layer 26U of the core 26, taking into account any sagging or festooning of the upper layer 26U and any intrusion of loose fibers from the core 26 into this space. It is important this minimum space between the upper and lower layers 26U and 26L is maintained under the loading of the wearer's weight while the wearer is sitting. The spacer 54 may be wrapped with a nonwoven fabric to reduce breakage or cracking of the spacer 54 and improve adhesive joining to other components.

The spacer 54 may be made of any material rigid enough to support the weight of the wearer and retain the aforementioned minimum clearance between the upper layer 26U and the lower layer 26L, but yet not provide enough resistance to compression to allow significant red marking of the skin to occur. A spacer 54 having approximately 10 percent compression under a Z-direction compressive pressure of about 1,400 kilograms per square meter (2 pounds per square inch) and which exhibits at least a 90 percent recovery has been found to work well. The spacer 54, provides a space between the upper and lower layers of the core 26 of at least about 0.6 centimeters when the spacer 54 is under a pressure of about 1,400 kilograms per square meter.

The spacer 54 may be made of any foam type material, with open cell foams being preferred over closed cell foams. This preference is because open cell foams generally minimize occurrences of red marking on the skin of the wearer.

Suitable materials for the spacer 54 include high internal phase emulsion foam absorbent materials. High internal phase emulsion foam absorbent materials may be made in accordance with the teachings of commonly assigned patent application Ser. No. 07/743,947, Issue Batch No. U40, filed Aug. 12, 1991 in the names of DesMarais et al., which patent application is incorporated herein by reference for the purpose of illustrating one suitable material for constructing a spacer 54 according to the present invention.

High internal phase emulsion foam absorbent material spacers 54 provide the advantages of high compressive resistance and breathability to reduce red marking. Furthermore, high internal phase emulsion foam absorbent materials are very absorbent, adding to the total capacity of the disposable absorbent article 20 and minimizing urine leakage.

However, high internal phase emulsion foam materials have certain disadvantages when used to construct the spacer 54. For example, certain of these materials may not readily bend along the major axis, making it difficult for the disposable absorbent article 20 to conform to the shape of the buttocks of the wearer. Further, these materials may be hard to machine or otherwise provide in the desired configuration and can be difficult to adhere to other components of the disposable absorbent article 20.

A rubber spacer 54 may also be utilized. If rubber spacer 54 is selected, suitable cross linked natural foam rubber sold by the Fulflex Company of Bristol, R.I. under the designation XNRF has been found suitable.

A rubber spacer 54 provides the advantage of being very flexible along the longitudinal axis LL of the spacer 54. However, a rubber spacer 54 has the disadvantages of being neither breathable nor absorbent, and is often too compressible.

If desired, cross-linked polyethylene foams may be utilized for the spacer 54. Suitable foams are sold by the Voltek Company, a division of Sekisui of Lawrence, Mass. as Type S foam. These foams provide the advantages of being inexpensive and easy to mold or otherwise machine to the desired configuration. However, these foams provide the disadvantages of not being breathable and are also often being too incompressible.

It will be apparent to one skilled in the art that several other materials are suitable for making the spacer 54 according to the present invention. For example, fast acting fluid stable aggregates as disclosed in commonly assigned U.S. Pat. application Ser. No. 07/705,451, Issue Batch No. T39, filed May 24, 1991 in the names of Roe et al., or twisted, chemically stiffened cellulosic fibers as disclosed in commonly assigned U.S. Pat. No. 4,898,642 issued Feb. 6, 1990 to Moore et al., are feasible, which patent application and patent are incorporated herein by reference for the purpose of disclosing alternative materials suitable for constructing spacer 54 according to the present invention. Prophetically, the spacer 54 according to the present invention may be made of the aforementioned Fibersorb brand material sold by the Atlantic Richfield Company.

Prophetically, there are several feasible ways to incorporate dual spring rates into the spacer 54, in addition to those noted above. For example, a spacer 54 which is symmetric about both its longitudinal and transverse axes LL and TT may be utilized but have different spring rates due to different radial thicknesses at different portions of the spacer 54, which thicknesses changes the function of the longitudinal position of the spacer 54. Alternatively, a spacer 54 symmetric about both the longitudinal and transverse axes LL and TT may have dual spring rates by having different thicknesses in the Z-direction. For example, the spacer 54 may monotonically taper in Z-direction thickness as a function of position along the longitudinal axis LL.

Similarly, a spacer 54 symmetric about both the longitudinal and transverse axes LL and TT may be made of bicomponent materials, utilizing stiffer materials or reinforcing members in that portion of the spacer 54 desired to have the greater transverse spring rate.

Yet another manner in which the dual spring rates may be incorporated into the spacer 54 is to provide different degrees of attachment of the spacer 54 to the other components, such as the topsheet 22, backsheet 24, or core 26 along various longitudinal positions of the spacer 54. For example, the portion of the spacer disposed towards the rear waist margin 34 may be firmly affixed to another component, such as the core 26 which provides transverse rigidity. The portion of the spacer 54 disposed towards the front waist margin 32 may be disconnected from or hingedly connected to the other components, allowing the front portion of the spacer to transversely articulate with very large deflection in response to a unit force. Such a spacer 54 need not be a closed figure, but may merely have one or more longitudinal spans 58.

In yet another embodiment, the spacer 54 may be bifurcated along the longitudinal axis LL. The end of the spacer 54 disposed towards the front waist margin 32 has a transverse span 56 on each side of the longitudinal axis LL, which transverse span 56 does not touch the symmetrically opposite transverse span 56 on the other side of the longitudinal axis LL. Similarly, the end of the spacer 54 disposed towards the rear waist margin 34 has a transverse span 56 on each side of the longitudinal axis LL, but which does not touch the symmetrically opposite transverse span 56 on the opposite side of the longitudinal axis LL.

The discontinuity between the transverse spans 56 oriented towards the rear waist margin 34 is smaller than (having a lesser transverse dimension) than the discontinuity between the transverse spans 56 oriented towards the front waist margin 32. This difference in discontinuities allows for greater transverse deflection in response to unit force (and hence lesser spring rate) of the end of the spacer 54 disposed towards the front waist margin 32 than the end of the spacer 54 disposed towards the rear waist margin 34. This difference in transverse deflection (and hence spring rates) occurs because once the lesser transverse discontinuity between the transverse spans 56 oriented towards the rear waist margin 34 is taken up by the deflection of each transverse span 56 towards the other, this end of the spacer 54 becomes very rigid and approximates a closed figure.

Conversely, the transverse spans 56 oriented towards the front waist margin 32 have not yet deflected sufficiently to take up the entire transverse discontinuity between the opposing transverse spans 56, and deflection may continue in response to the same unit force. Thus, a difference in spring rates between the ends of the spacer 54 is realized, because deflection at the end of the spacer 54 oriented towards the rear waist margin 34 is dramatically decreased in response to unit force after that end of the spacer 54 has been transversely deflected a certain distance.

In yet another alternative, a spacer 54 according to the present invention may have three or more different spring rates rather than only two spring rates as discussed above. The advantage of incorporating three or more spring rates into the spacer 54 is the portion 57 of the spacer 54 longitudinally intermediate the transverse and longitudinal spans 56 and 58 discussed above and having a spring rate which is between the spring rates of the transverse and longitudinal spans 56 and 58 discussed above provides for transition between such transverse and longitudinal spans 56 and 58 and for controlled transverse collapse of the spacer 54.

The spacer 54 may be modified to accommodate the curvature of the buttocks of the wearer. For example, the spacer 54 may be transversely slit or otherwise provided with transversely oriented score lines on the tension side of the neutral axis of the spacer 54. The tension side of the spacer 54 is dictated by the curvature of the spacer 54 around the buttocks of the wearer and is the side of the spacer 54 facing the backsheet 24. This arrangement allows the spacer 54 to curve along its longitudinal dimension and to more readily and accurately conform to the buttocks of the wearer. This arrangement may also make the disposable absorbent article 20 easier to fold for packaging and shipment.

Of course, it will be apparent to one skilled in the art that several of the aforementioned means for providing dual spring rates may be combined into a spacer 54 having multiple radii of curvature, multiple radial thicknesses, multiple Z-direction dimensions, bicomponent materials, and multiple orientations of longitudinally and transversely oriented spans 56 and 58 and discontinuities. Similarly, such means for providing dual spring rates may be utilized with a spacer 54 which is not symmetric about its transverse axis TT. It will be apparent that several other modifications and variants may be made by one skilled in the art. All are within the scope and intent of the appended claims.

What is claimed is:

1. A disposable absorbent article having a front waist margin, a rear waist margin, and a longitudinal axis, said disposable absorbent article further comprising:

a liquid impervious backsheet;

a liquid pervious topsheet at least partially peripherally joined to said backsheet to form a void space intermediate said topsheet and said backsheet;

an absorbent core intermediate said topsheet and said backsheet; and a spacer intermediate said topsheet and said backsheet and joined to one of said topsheet, said backsheet and said core for maintaining the remainder of said void space unoccupied by said spacer and said core between said topsheet and said backsheet for receiving fecal material while the article is being worn, said spacer being generally symmetric about said longitudinal axis, the shape of said spacer defining two transverse spans, a larger transverse span and a smaller transverse span, said larger and smaller transverse spans being disposed at longitudinally opposite ends of said spacer, said spacer being oriented so that said larger transverse span is disposed towards said rear waist margin and said smaller transverse span is disposed towards said front waist margin;

said liquid pervious topsheet having an aperture centered on said longitudinal axis and registered with said spacer for communicating liquid and solid fecal material to said remainder of said void space;

said absorbent core comprising an upper layer joined to said topsheet and a lower layer joined to said backsheet, said spacer is joined to one of said upper layer and said lower layer in a disposition intermediate said upper layer and said lower layer such that said upper layer and said lower layer have a space therebetween of at least about 0.6 centimeters when said spacer is under a pressure of about 1.400 kilograms per square meter, said lower layer comprising air felt intermediate said spacer and said backsheet and devoid of a cavity or cutout therein registered with said spacer for receiving said fecal material.

2. A disposable absorbent article according to claim 1 wherein said spacer is composed of a material selected from the group consisting of foam, rubber, twisted cellulosic fibers, and fluid stable aggregates.

3. A disposable absorbent article according to claim 1 wherein said topsheet is elastically extensible.

4. A diaper having front waist margin, a rear waist margin, and a longitudinal axis, said diaper further comprising:
- a liquid impervious backsheet;
- a liquid pervious topsheet at least partially peripherally joined to said backsheet to form a void space intermediate said topsheet and said backsheet;
- an absorbent core intermediate said topsheet and said backsheet; and
- a spacer intermediate said topsheet and said backsheet and joined to one of said topsheet, said backsheet and said core for maintaining the remainder of said void space unoccupied by said spacer and said core between said topsheet and said backsheet for receiving fecal material while the diaper is being worn,
- said spacer having a longitudinal axis and being symmetric thereabout, and said spacer further having a transverse axis orthogonal to said longitudinal axis, said transverse and longitudinal axes defining transverse and longitudinal directions, respectively, said spacer comprising two opposed radii of curvature, each radius of curvature having a concavity oriented in the longitudinal direction, and defining first and second portions of a generally closed figure,
- said first and said second portions of said generally closed figure each spanning said longitudinal axis, one said radius of curvature being greater than the other said radius of curvature, so that there are both greater and lesser radii of curvature, said radii of curvature being at longitudinally opposite ends of said spacer, said two portions of said generally closed figure defined by said two radii of curvature being joined by at least two longitudinally oriented spans of said spacer, one said longitudinally oriented span of said spacer being on each side of said longitudinal axis;
- said liquid pervious topsheet having an aperture centered on said longitudinal axis for communicating liquid and solid fecal material to said remainder of said void space;
- said absorbent core comprising at least one layer which includes air felt, said at least one layer being intermediate said spacer and said backsheet and devoid of a cavity or cutout therein registered with said spacer for receiving said fecal material.

5. A diaper according to claim 4 wherein each said longitudinally oriented span of said spacer has a radius of curvature and a concavity oriented away from said longitudinal axis.

6. A diaper according to claim 5 wherein said spacer has a greater radial thickness in said portion of said spacer comprising the greater radius of curvature than in said portion of said spacer comprising the lesser radius of curvature.

7. A diaper according to claim 6 wherein said greater radius of curvature is at least about 3.6 centimeters.

8. A diaper according to claim 6 wherein said lesser radius of curvature is less than about 1.5 centimeters.

9. A diaper having a front waist margin, a rear waist margin, and a longitudinal axis, said diaper further comprising:
- a liquid impervious backsheet;
- a liquid pervious topsheet at least partially peripherally joined to said backsheet to form a void space intermediate said topsheet and said backsheet;
- an absorbent core intermediate said topsheet and said backsheet; and
- a spacer joined to said topsheet and disposed intermediate said topsheet and said backsheet for maintaining the remainder of said void space unoccupied by said spacer and said core between said topsheet and said backsheet for receiving fecal material while the diaper is being worn,
- said spacer having a longitudinal axis and being symmetric thereabout, and said spacer further having a transverse axis orthogonal to said longitudinal axis, said transverse and longitudinal axes defining transverse and longitudinal directions, respectively, said spacer comprising two opposed radii of curvature, each having concavity oriented in the longitudinal direction, and defining first and second portions of a generally closed figure, said first and said second portions of said generally closed figure each spanning said longitudinal axis, one said radius of curvature being greater than the other said radius of curvature, so that there are both greater and lesser radii of curvature, said radii of curvature being at longitudinally opposite ends of said spacer, said two portions of said generally closed figure defined by said two radii of curvature being joined by at least two longitudinally oriented spans of said spacer, one said longitudinally oriented span of said spacer being on each side of said longitudinal axis;
- said liquid pervious topsheet having an aperture centered on said longitudinal axis for communicating liquid and solid fecal material to said remainder of said void space;
- said absorbent core comprising at least a lower layer which includes air felt, said lower layer intermediate said spacer and said backsheet and devoid of a cavity or cutout therein registered with said spacer for receiving said fecal material.

10. A diaper according to claim 9 wherein said absorbent core further comprises an upper layer joined to said topsheet and wherein said lower layer is joined to said backsheet, said spacer being joined to one of said upper layer and said lower layer in a disposition intermediate said upper layer and said lower layer.

11. A diaper according to claim 10 wherein said topsheet is elastically extensible.

* * * * *